(12) United States Patent
Daxer (10) Patent No.: US 12,268,592 B2
(45) Date of Patent: Apr. 8, 2025

(54) CORNEA IMPLANT

(71) Applicant: Albert Daxer, Wilhering (AT)

(72) Inventor: Albert Daxer, Wilhering (AT)

(*) Notice: Subject to any disclaimer, the term of this patent is extended or adjusted under 35 U.S.C. 154(b) by 833 days.

(21) Appl. No.: 17/600,206

(22) PCT Filed: Mar. 30, 2020

(86) PCT No.: PCT/EP2020/058980
§ 371 (c)(1),
(2) Date: Sep. 30, 2021

(87) PCT Pub. No.: WO2020/201221
PCT Pub. Date: Oct. 8, 2020

(65) Prior Publication Data
US 2022/0202562 A1 Jun. 30, 2022

(30) Foreign Application Priority Data
Apr. 1, 2019 (AT) .................................. A 120/2019

(51) Int. Cl.
*A61F 2/14* (2006.01)
(52) U.S. Cl.
CPC ...... *A61F 2/147* (2013.01); *A61F 2210/0014* (2013.01); *A61F 2240/001* (2013.01); *A61F 2250/0015* (2013.01); *A61F 2250/0029* (2013.01)
(58) Field of Classification Search
CPC .............. A61F 2/147; A61F 2210/0014; A61F 2240/001; A61F 2250/0015; A61F 2/142; A61F 2/145; A61F 2250/0028; A61F 2250/0029
See application file for complete search history.

(56) References Cited

U.S. PATENT DOCUMENTS

| 8,092,526 B2 | 1/2012 | Daxer |
| 2002/0010510 A1 | 1/2002 | Silvestrini |
| 2009/0076601 A1 | 3/2009 | Daxer |

FOREIGN PATENT DOCUMENTS

| WO | 93/14703 A1 | 8/1993 |
| WO | 97/28759 A1 | 8/1997 |

OTHER PUBLICATIONS

Albert Daxer, "Biomechanics of Corneal Ring Implants", Basic Investigation, Cornea, vol. 34, No. 11, Nov. 2015, pp. 1493-1498.
Albert Daxer and Peter Fratzl, "Collagen Fibril Orientation in the Human Corneal Stroma and its Implication in Keratoconus", Investigative Ophthalmology & Visual Science, Jan. 1997, vol. 38, No. 1, pp. 121-129.
International Search Report in PCT/EP2020/058980, mailed Jul. 16, 2020.

*Primary Examiner* — Javier G Blanco
(74) *Attorney, Agent, or Firm* — Collard & Roe, P.C.

(57) ABSTRACT

The present invention relates to a ring-shaped implant having shape memory for implantation in the cornea of the eye, wherein the implant spans an implant plane in a starting state, and wherein the implant is transferable by application of a compression force (F) in the implant plane (8) from a starting state into an intermediate state, in which the lateral dimensions of the implant, measured in the force direction, are smaller than in the starting state, wherein it is provided according to the invention that the alignment of an implant cross-section (1) in the intermediate state is pivoted at least in one pivotable longitudinal section of the implant by an angle (α) in relation to the starting state.

14 Claims, 3 Drawing Sheets

CORNEA IMPLANT

CROSS REFERENCE TO RELATED APPLICATIONS

This application is the National Stage of PCT/EP2020/058980 filed on Mar. 30, 2020, which claims priority under 35 U.S.C. § 119 of Austrian Application No. A 120/2019 filed on Apr. 1, 2019, the disclosure of which is incorporated by reference. The international application under PCT article 21(2) was not published in English.

The present application relates to a ring-shaped implant having shape memory for implantation in the cornea of the eye, wherein the implant spans an implant plane in a starting state, and wherein the implant is transferable by application of a compression force in the implant plane from a starting state into an intermediate state, in which the lateral dimensions of the implant, measured in the force direction, are smaller than in the starting state.

PRIOR ART

The refractive power of the eye is dependent by approximately 70% on the central curvature of the cornea front face. Therefore, most treatments of defective vision are based on changing the central radius of curvature. For example, in the case of a myopic eye, if one wishes to reduce the refractive power of the eye, for example, to enable seeing without a visual aid, the central radius of curvature of the cornea front face has to be increased and its central curvature thus has to be reduced. To achieve this, for example, tissue can be removed from the cornea using an excimer laser, specifically more in the center of the cornea than farther peripherally. The same effect can be achieved by introducing a volume in the form of a ring-shaped implant into the cornea in the periphery. In this case, the corneal tissue in the periphery where the implant has been introduced has to take a "detour" around the thickness of the implant, which results in a central shortening of the arc length and thus flattening of the cornea front face. In any case, however, the weakening of the cornea due to the treatment of the cornea can represent a problem. In the case of laser removal, it is simply the tissue loss and in the separate special case of LASIK, where in addition a corneal flap has to be prepared, it is also this which weakens the cornea. In any case, the corneal thickness and the number of diopters which have to be removed sets limits on the extent of the laser removal (removal depth). In the case of corneal implants in the form of ring segments (incomplete ring), a radial incision is to be executed, which weakens the cornea. Because of the incision profile, which is perpendicular to the surface, it would gape open. It is therefore necessary to close this radial incision with a suture, which additionally impairs the comfort, the predictability, and the safety of the intervention. Ring segments are introduced into a circular tunnel so that they are not in a biomechanical equilibrium with the corneal tissue. In addition, the ring segments have ends which can cause a high pressure locally on the tissue. For all of these reasons, ring segments are subject to sometimes significant postoperative complications. To solve these problems, U.S. Pat. No. 8,092,526 B2 describes a ring-shaped implant (full ring) extending over a complete ring circumference of 360°, which in contrast to segmented implants (ring segments) is not introduced in a circular tunnel, but in a corneal pocket. The access to the corneal pocket, via which the full ring is introduced, is laminar and in principle is biomechanically neutral if it does not exceed a certain dimension of approximately 5-6 mm. Ideally, the access is to be as narrow as possible so as not to influence the biomechanics of the cornea. These biomechanical principles are discussed in Daxer A. *Biomechanics of Corneal Ring Implants. Cornea* 2015; 34:1493-1498. Since the material of the ring implants is to be as rigid as possible to stabilize the desired corneal geometry, the problem exists that the full ring can break in the event of excessively strong compression. The full ring described in U.S. Pat. No. 8,092,526 B2 is distinguished by a shape memory, according to which its diameter can be compressed to a certain extent to be able to introduce it through the narrowest possible access into the corneal pocket, where it then assumes the original circular form again to fulfill its function. The risk of breaking is reduced according to U.S. Pat. No. 8,092,526 B2 in that the implant is embodied so that the ring component which is located at 90° to the compression force is deflected out of the ring plane upon compression, whereby a further degree of freedom can be obtained against the risk of breaking. The compression force is partially converted here into elastic deformation energy which is stored in the deflected part of the ring at 90° to the compression force direction. Due to the deflection of this ring part located orthogonal to the force direction, instead of an oval geometry, a saddle-shaped geometry of the ring is achieved, which requires a certain dexterity of the operator during the implantation, since the implant cannot simply be pushed straight through the opening into the cornea, but rather along a curved curve, which approximately has to correspond to the now curved shape of the deformed ring plane. It would be desirable if one could compress the implant without such a strong modification of the oval shape into a steep saddle occurring at the same time and without the rigid implant breaking during the compression. It would also be desirable that one could possibly compress the saddle shape still further than is possible by way of the invention of U.S. Pat. No. 8,092,526 B2.

OBJECT OF THE INVENTION

It is the object of the invention to overcome these problems of the prior art and to provide an improved corneal implant which enables implantation into the cornea through a narrow wound opening, without the implant breaking, and permitting permanent safe application on the eye for refractive power correction.

DESCRIPTION OF THE INVENTION

The object is achieved by a ring-shaped implant having shape memory for implantation in the cornea of the eye, wherein the implant spans an implant plane in a starting state, and wherein the implant is transferable by application of a compression force in the implant plane from a starting state into an intermediate state, in which the lateral dimensions of the implant, measured in the force direction, are smaller than in the starting state, wherein it is provided according to the invention that the alignment of an implant cross-section in the intermediate state is pivoted, at least in a pivotable longitudinal section of the implant, by an angle in relation to the starting state.

In principle, the pivotable longitudinal section of the implant can extend along the entire circumferential length of 360° of the ring-shaped implant, but at least in sections over preferably at least 5°, better at least 10°, and ideally at least 15°. Multiple pivotable longitudinal sections thus each also extend at least over 5°, better at least over 10°, and ideally at least over 15° along the circumference of 360° of the implant.

A pivotable or the pivotable longitudinal section can also preferably be located in the region of the point of engagement of the compression force. It would be conceivable here that the implant has a corresponding marking which indicates where the compression force is to engage. At least one other longitudinal section would then be embodied to be non-pivotable.

The implant according to the invention can be manufactured in principle from any material, as long as it meets the properties according to the invention and is suitable and permitted as an implant material for permanent implantation in a human body. It can thus be embodied, for example, from metal (for example titanium, etc.) or plastic (for example PMMA) or biological materials (for example collagen). The material can be transparent or opaque. It can have an arbitrary color. It is preferably manufactured from transparent plastic or embodied in blue, brown, or green color, to not be able to be identified as a foreign body in the eye from the outside and/or to delimit the optical (not the anatomical) entry pupil for the purpose of reducing higher-order imaging errors (for example, spherical aberration, coma, etc.). The material is to be as rigid as possible to permanently enable the refractive force correction in a stable manner, in that the implant can apply a certain basic shape (curvature) to the cornea. It is therefore preferably to have a modulus of elasticity of at least 1000 MPa, better at least 2000 MPa, and ideally greater than 3000 MPa. If it is embodied as a thermoplastic, the water absorption is not to exceed 5%, better 2%, and the water content is therefore to be less than 2% if possible. A continuous service temperature of at least 50° C., better 60° C., and ideally at least 70° C. would be reasonable. Materials having such properties often only have a minor fracture elongation (elongation upon fracture), i.e., of only a few percent.

The implant can in principle also have any suitable shape. Nonetheless, an essentially ring-shaped implant is particularly advantageous. The ring-shaped implant can be embodied both as closed and also open, i.e., as a continuous ring or as an interrupted ring.

The implant plane according to the invention is considered to be the plane which is delimited either by an outer edge or an inner edge of the implant. The (convex) delimitation curved away from the implant represents the outer edge. I.e., in the case of the provision of an essentially ring-shaped implant, thus an implant having a central opening, the outer edge of the implant is the circumferential line which, viewed from a circle center point (for example center point of the implant 9' in FIG. 6), is farthest away from this center point, while the inner edge is the circumferential line of the implant which, viewed from a circle center point (for example center point of the implant 9') is located closest to this center point.

The implant according to the invention can be in multiple states, namely in a starting state, an intermediate state, and an end state.

The starting state is the state in which the implant is shaped before it is transferred by the action of a compression force into the state in which it can be implanted. This means that in the starting state the implant has greater lateral dimensions in the normal case than during the implantation process. In general, the lateral dimension in the starting state will not be greater than 10 mm.

The intermediate state is the state into which the implant is transferable from the starting state by the action of a trigger and in which it can be implanted. This is performed, for example, by application of a compression force to one or more sections of the implant, whereby the lateral dimensions of the implant are reduced. It is advantageous if a lateral dimension of the implant in the intermediate state is not greater than 6 mm.

After implantation in the cornea, the implant can be transferred further into an end state. The end state is the state in which the implant remains after implantation in the cornea. The end state preferably essentially corresponds to the starting state of the implant. However, it is not precluded that the end state is also a state deviating from the starting state (a deviating geometry) of the implant.

A sectional surface (area) of the implant (also referred to as an implant body hereinafter) is referred to as the implant cross-section (also referred to as the cross-sectional area hereafter), which is in a plane which is parallel to the axis of symmetry (also referred to as hereinafter as the ring axis or rotational axis or axis of rotation) of the implant, in particular which extends through or in parallel to the axis of symmetry.

The implant plane is perpendicular to the axis of symmetry of the implant at least in the starting state.

The implant cross-section of the implant can be embodied as desired in each case, e.g., circular, oval, as a polygon with or without rounded edges, convex on one side and straight or concave on the other, etc. The implant can be curved as desired along a circumferential axis (also referred to as an axis, center line, center axis, body axis, or longitudinal axis) of the implant. However, in the starting state, this body axis preferably follows a constant curvature around an axis of symmetry (also referred to as axis of rotation) having an arc length of 360°. In the case of an implant having circular design, the circumferential axis would be a circle and the implant body would be a ring. If the implant is additionally a torus, the circumferential axis would form the center point of all implant cross-sections, which would then be circles.

The implant can have a variable or homogeneous implant cross-section along the circumferential axis. A homogeneous cross-section means that the implant cross-section is the same at any arbitrary point, while a variable cross-section means that the cross-section differs in different regions of the implant. In the case of a homogeneous implant cross-section, the cross-sectional shape, the alignment of the implant cross-section to the implant plane, and also the size of the cross-sectional area along the circumference are all the same.

The implant can be geometrically complete in that it extends over 360° arc length. The implant can be mechanically incomplete or complete. A mechanically complete implant has no ends and is embodied as a completely closed ring. A mechanically incomplete implant is also embodied geometrically over an arc length of 360°, but has a discontinuity, thus a mechanical interruption, and therefore ends. These ends can have an arbitrary geometry in this case. The ends ideally overlap.

Implants having shape memory are already known in the prior art, which permit an at least temporary reduction of the lateral dimensions of the implant by the transfer into the intermediate state. Nonetheless, an increased risk of breaking of the implant often accompanies this reduction of the lateral dimensions, since the materials of the implants of the prior art cannot withstand the acting forces.

The object is achieved according to the invention in that the alignment of the implant cross-section is pivoted at least in sections by an angle α in relation to the starting state. The rotation of the implant cross-section is achieved, for example, by the action of a compression force on the implant. This rotation causes the lateral dimensions of the implant to be reduced still further in relation to a compression alone, whereby the implant can be implanted via smaller openings in the cornea.

To be able to use the above-mentioned implant materials for the present invention, it is necessary to prevent these materials from breaking in the event of a compression as much as possible. In principle, upon compression of the mentioned materials, fractures occur due to the material fatigue or lack of (pseudo-)elasticity in loaded implant regions in the event of excessively strong compression. This results, on the one hand, from the compaction of the material in the longitudinal section, which is at 90° to the direction of the force action, in the interior of the implant or in the region of the inner edge of the implant and, on the other hand, in the tension forces which act in the longitudinal section, which is at 90° to the direction of the force action, on the outer side, in particular in the region of the outer edge of the implant. To prevent the breaking of the implant according to the invention, in the present invention, for example, a rotation of the implant cross-section in a longitudinal section region along the circumference, which is preferably located at the point of the force action, is achieved by the acting compression force. It is thus made possible for the implant to tolerate a greater force action without breaking than in the event of force action without rotation of the implant cross-section in this pivotable longitudinal section.

To be suitable as a material for an implant according to the invention, it has to be a material having specific shape memory. Such materials are already sufficiently known in the prior art.

The pivoting at least in sections of the implant body along or around a circumferential axis in the intermediate state, triggered by an external signal, such as the action of a compression force, is achieved here in that a shape memory is applied at least in sections to the implant body, preferably during the manufacturing, which ensures that upon application of a compression force, the desired pivot of the implant body, preferably around a circumferential axis, takes place at least in a specific longitudinal section of the implant.

The application of a shape memory can be carried out by a mechanical, thermal, electrical, or another physical or chemical treatment of the material or the implant, preferably, but not necessarily, during the production. The implant can be manufactured in principle from any material including plastic, metal, semiconductor, insulator, ceramic, biological materials, etc. which enables such a treatment. Thus, for example, in the case of a polymer plastic, the alignment or arrangement of the polymer molecules can be embodied in such a way that an externally applied compression force results in a force distribution in the interior of the implant body from which the desired pivot of the implant body results. The arrangement or alignment or size distribution of the polymer molecules along the circumference or inside the implant cross-section can also vary at least in sections along the circumference, for example. Thus, for example, the alignment of the polymer molecules can be embodied at least in sections in parallel to or circularly around a circumferential axis. Furthermore, for example, the desired pivot can also be achieved by variation of the material density along the circumference or over the cross-section. Materials to which a specific shape may be applied, for example, by a second-order phase transition (martensitic phase transition) by thermal or other physical treatments under application of a compression force in the meaning of a shape memory material and in the case of which the pivot is triggered in the application by application of a corresponding compression force are also conceivable.

It is therefore necessary for the materials which are used for producing the implant according to the invention to be able to be present at least in two phases, whereby precisely the shape memory according to the invention is provided. The conversion from the one phase into the other phase is triggered by an external trigger, such as an acting force or temperature. The crystal structure of the molecules of the material used for the implant can be present in two phases and can be constructed differently in these phases, i.e., the molecules in one phase have a different arrangement, alignment, and/or size distribution than in the other phase. Materials having both thermal and mechanical shape memory can be used for the invention.

It can also be provided that a pivotable longitudinal section is located along the circumference of the implant outside the engagement point of the compression force.

To be able to particularly effectively reduce the lateral dimensions of the implant in the intermediate state, it is provided in one embodiment of the invention that the implant has two pivotable longitudinal sections opposite to one another in the implant, the implant cross-sections of which in the intermediate state are each pivoted by an angle in relation to the starting state. It can be provided, for example, that these pivotable longitudinal sections are each located in the region of the engagement point of the compression force.

In this case, the compression force could be exerted in such a way that it consists of two oppositely oriented components of equal size, which are applied on opposite sides of the implant. The two opposite longitudinal sections have the effect that upon an action of an external signal, such as a compression force, both longitudinal sections rotate by an angle α, whereby, on the one hand, the lateral dimensions of the implant are reduced still further and, on the other hand, the breaking of the implant is prevented in the two particularly stressed longitudinal sections. The two pivotable longitudinal sections opposite to one another can be arranged, for example, at an angle of 90° to the engagement point of the compression force. The one pivotable longitudinal section could also be provided in the engagement point of the compression force, however, while the other would then be arranged opposite to the engagement force of the compression force.

Of course, it is not precluded that the implant has more than two longitudinal sections, such as 3, 4, or 5 longitudinal sections, in which a rotation by the angle α occurs. It is also not precluded that the implant has multiple pairs of opposite longitudinal sections, which rotate by an angle α upon action of an external signal.

An implant of suitable size is thus achieved, which enables a user to insert the implant through a particularly small corneal gap into the cornea, whereby complications which accompany such an implantation can be avoided as much as possible.

One embodiment of the implant is that it contains polymer material, in particular that it is manufactured from polymer material. In order to achieve that the implant is particularly compatible for the patient and is not rejected by the body, it is provided in one embodiment of the invention that the implant is manufactured from a biocompatible polymer material.

Biocompatible means that the materials used for the manufacturing of the implant, which are in direct contact with living tissue, do not exert any negative influence on their metabolism. Examples of biocompatible materials which can be used for manufacturing the implant are the above-mentioned materials. The implant can thus be made of a polymer plastic, such as PMMA. It is also not precluded that the implant comprises two materials, wherein the material that is in direct contact with the living tissue, thus the cornea, is manufactured from biocompatible material. Of course, it is also not precluded that the implant consists of a material which is not a polymer, as long as this material is biocompatible, for example metals, such as titanium, and has a shape memory according to the invention.

Polymers typically consist of elongated or long-chain molecules (polymer molecules), which are always constructed from the same monomer molecule, arranged in succession, and which, essentially similar to a cylinder, have a longitudinal extension and a transverse extension perpendicular to the longitudinal extension. The longitudinal extension (length of the polymer molecule) is typically greater than the transverse extension (diameter) in this case. The direction in which the longitudinal extension of a polymer molecule faces is the alignment of the polymer molecule in relation to a defined reference axis. Such a reference axis can be, for example, in the case of the implant according to the invention, the circumferential axis, thus the longitudinal axis of the implant along the circumference of the implant. The alignment of the polymer molecules can take place mostly in a specific direction or evenly distributed in all directions (random oriented). The measurement of the alignment of the polymer molecules in space in relation to a reference axis can be measured, for example, by the diffraction of electromagnetic waves on the molecules (A. Daxer and P. Fratzl. Collagen Fibril Orientation in the Human Corneal Stroma and its Implication in Keratoconus. Investigative Ophthalmology and Visual Science. 1997; 38:121-129).

The polymer molecules in the implant can have a preferred orientation or preferred direction at least in sections along the ring circumference of the implant. This means that more polymer molecules face with their longitudinal extension in the preferred direction than in another direction. This preferred orientation of the polymer molecules can be, for example, the longitudinal axis or circumferential axis of the implant or also the circumference of the cross-section, or in principle any arbitrary other direction.

However, the polymer molecules can themselves also be shaped curved or linear. The arrangement of the polymer molecules and their alignment can display a specific course pattern at least in sections along the circumference of the implant, for example, in that they follow a specific pattern in the majority. The polymer molecules could thus be arranged helically, for example, in that they are arranged and aligned at least in sections mostly in a helix along the circumference of the implant, thus around the circumferential axis. However, they could also be aligned circularly around the circumferential axis at least mostly. In the case of an at least sectional spiral or helical arrangement or alignment of the polymer molecules, it is dependent, for example, on the "pitch height" of the turns whether the alignment of the polymer molecules is aligned mostly in parallel to the circumferential axis or perpendicular thereto around the circumferential axis.

For example, an arrangement or alignment of the polymer molecules at least in sections along the circumferential axis of the implant can be generated in that the liquid, heated mass made of polymer material which is poured into a container rotates around a specific axis during the cooling phase into the solid state, either using a stirrer or by rotation of the container around an axis. Different alignment, arrangement, or size distributions of the molecules along the circumference in sections can also be implemented by suitable cutting of discs out of the cold solid block of polymer and subsequent turning of the ring implants out of the discs. Instead of circular rotation forces, the material can also be subjected during the cooling to other forces, for example acceleration forces, to achieve a specific distribution of different molecule sizes or molecule arrangements or molecule alignments along the circumference or over the cross-section of the ring implant.

The invention accordingly also comprises a method for producing an implant according to the invention, wherein a specific alignment and/or arrangement and/or size distribution of polymer molecules is produced in a polymer material before the solidification by action of an acceleration force (e.g., by rotation, linear acceleration, gravitation), the polymer material is caused to solidify in this state, and subsequently the implant is manufactured from this solidified polymer material.

To achieve a particularly good breaking strength of the implant, it is provided in one embodiment of the invention that the arrangement and/or the alignment and/or the size distribution of the polymer molecules of the polymer material, which is biocompatible in particular, is embodied in a specific manner at least in sections along the circumferential axis of the implant or over the cross-section of the implant. Thus, for example, the polymer molecules can be aligned in a preferred direction at least in sections along the circumference of the implant, in particular around the entire circumference, depending on the remaining structure, for example, either mostly in the direction of the longitudinal axis along the circumference (the circumferential axis) or also mostly not in the direction of the longitudinal axis along the circumference (the circumferential axis). Thus, for example, in the case of a helical or circular arrangement of polymer molecules, depending on the pitch angle of the helical course, the polymer molecules can be arranged mostly either in the direction or not in the direction of the longitudinal axis along the circumference. The polymer molecules are then arranged mostly in the direction of the longitudinal axis along the circumference if the projection of the polymer molecules on the longitudinal axis in particular is greater than on any direction perpendicular to the longitudinal axis. Vice versa, it also applies that the polymer molecules are then not aligned mostly along the longitudinal axis along the circumference if the projection of the polymer molecules in a direction perpendicular to the longitudinal axis is greater than in the direction of the longitudinal axis. Strictly speaking, the direction of the longitudinal axis is to be understood here as the direction of the tangent on the longitudinal axis at a specific point along the circumference of the implant, since the longitudinal axis is curved around the implant center point or around the axis of rotation of the implant.

To achieve a particularly good breaking strength of the implant, it is provided in another embodiment of the invention that the arrangement and/or the alignment and/or the size distribution of the polymer molecules of the polymer, which is biocompatible in particular, is different along the circumference of the implant or within the implant cross-section in various longitudinal sections of the implant. The arrangement and/or the alignment and/or the size distribution of the polymer molecules of the polymer, which is biocompatible in particular, can thus be different along the circumference of the implant or within the implant cross-section in one pivotable longitudinal section of the implant from another longitudinal section of the implant.

A different arrangement and/or alignment and/or size distribution of the polymer molecules has the result that the breaking strength is higher in certain longitudinal sections than in other longitudinal sections. This means that in particular in those longitudinal sections which rotate due to a force action by an angle α from the starting state of the implant, a more advantageous arrangement, alignment, or size distribution of the polymer molecules than in other longitudinal sections is provided.

A different arrangement or alignment of the polymer molecules in various longitudinal sections is understood according to the invention to mean that, for example, in a first longitudinal section of the implant, the polymer molecules are aligned mostly in a specific direction relative to the circumferential axis of the implant and in another longitudinal section in another direction.

A different arrangement of the polymer molecules in various longitudinal sections is understood according to the invention to mean that, for example, in a first longitudinal section of the implant the majority of the polymer molecules has a different density (thus more molecules per volume) than in another longitudinal section.

A different size distribution of the polymer molecules in various longitudinal sections is understood according to the invention to mean that, for example, in a first longitudinal section of the implant, the majority of the polymer molecules have an essentially similar size which differs from the size of the majority of the polymer molecules of a second longitudinal section. The relative composition of monomers, oligomers, and polymers and/or the distribution of monomers, oligomers, and polymers in various longitudinal sections and/or over an implant cross-section can be different.

In other words, additionally or alternatively to the variation of the composition of monomers, oligomers, and polymers in various longitudinal sections of the implant, it can also be provided that the implant has a different distribution of monomer molecules, oligomer molecules, and polymer molecules on at least one longitudinal section along the circumference of the implant within the implant cross-section. Additionally or alternatively, it can also be provided that the implant has a different density and/or a different alignment of the polymer molecules along the circumference.

To obtain a particularly good breaking strength of the implant, it is provided in one embodiment of the invention that the alignment of the polymer molecules in at least one pivotable longitudinal section is largely circular around the circumferential axis of the implant and in at least another longitudinal section is largely parallel to the circumferential axis of the implant.

Because at least one longitudinal section has polymer molecules aligned in parallel to the circumferential axis and one longitudinal section has polymer molecules aligned circularly around the circumferential axis, the implant does not break in the event of an acting compression force. The circularly arranged polymer molecules cause improved elasticity of the material, so that the implant does not break upon action of the compression force.

To achieve a particularly good breaking strength of the implant, it is provided in one embodiment of the invention that the implant has a material density, which material density varies along the circumference of the implant and/or over the implant cross-section. This means, for example, that the material density is different in one pivotable longitudinal section of the implant from another longitudinal section of the implant. In particular, the material density can be less there.

The different material density in the implant has the result that longitudinal sections having a lower material density tolerate a higher material compaction due to acting compression forces, whereby the breaking strength of the implant can be increased. It is particularly advantageous if the regions having lower material densities are arranged at the points which are subjected to an increased load upon compression.

A variation of the material density along the implant cross-section has the effect that the implant permits a material compaction due to the acting compression force, on the one hand, and will also withstand the simultaneously acting tension forces, which are caused by the compression force, on the other hand, whereby the breaking strength of the implant is increased.

In one embodiment of the invention, it is provided that the implant has an implant cross-section deviating from rotational symmetry along the circumference of the implant in at least one longitudinal section of the implant, so that the implant cross-section is different in one pivotable longitudinal section of the implant from another longitudinal section of the implant to further increase the breaking strength of the implant.

Due to the implant cross-section deviating in at least one longitudinal section of the implant from rotational symmetry, upon the action of compression force, the implant pivots at the longitudinal section predetermined by the deviating implant cross-section, whereby, on the one hand, a deliberate reduction of the lateral dimensions of the implant is achieved and, on the other hand, the breaking of the implant is prevented by the rotation of the implant cross-section in a predetermined longitudinal section, since a better adaptation to the stresses of the material caused by the acting compression force is achieved in precisely this predetermined region by the change of the implant cross-section.

To increase the stability of the implant upon reduction of the lateral dimensions due to the acting compression force, it is provided in one embodiment of the invention that the implant is embodied in the starting state as a complete ring having uniform implant cross-section along the circumference of the implant rotationally symmetrical around an axis perpendicular to the implant plane.

Because the implant has the same implant cross-section on each longitudinal section of the implant, the implant is not rotated at a predetermined point upon action of compression force, but rather in principle can rotate in each longitudinal section of the implant. Greater freedom is thus given to the user, about where he acts on the implant by compression force, i.e., the user does not have to find the point suitable for the action of the compression force before reducing the lateral dimensions of the implant, but can have the compression force act on any arbitrary longitudinal section of the implant, since each longitudinal section withstands the increased stresses equally well.

Of course, however, it can nonetheless be provided that the arrangement and/or the alignment and/or the size distribution of the polymer molecules of the biocompatible polymer along the circumference of the implant or within the implant cross-section is different at least in sections along the circumference of the implant; or that the material density varies along the circumference of the implant and/or over the implant cross-section. In this way, again at least one suitable pivotable longitudinal section can be provided, which then has to be identified by a marking, however.

To ensure particularly simple application and a high level of wearing comfort of the implant, it is provided in one embodiment of the invention that the implant is both geometrically and also mechanically closed and does not have a discontinuity.

If the implant is embodied as both mechanically and also geometrically closed, the implant does not have ends which could act in some type of annoying way on the wearer of the implant. In particular, it is ensured by a geometrically and mechanically closed implant that the forces which act on the tissue are distributed on the entire circumference of the implant and are not concentrated at the ends.

In one embodiment of the invention, it is provided that the implant has an inner edge, which inner edge delimits a surface, wherein the surface delimited by the inner edge is planar in the starting state and is curved in the intermediate state.

It is possible due to the shape memory of the implant according to the invention that the implant can assume at least two states, but better three states, namely a starting state and an intermediate state and in the ideal state also an end state, wherein this end state preferably corresponds precisely to the starting state. To enable even smaller lateral dimensions of the implant and thus an implantation via an even smaller corneal gap, the formation of a saddle shape of the implant is achieved by an intermediate state in which the implant plane is no longer planar. The reduction of the lateral dimensions of the implant is achieved by the direction upward of two opposing longitudinal sections of the implant, while at the same time a high breaking strength of the material is ensured by the rotation of these longitudinal sections.

To achieve a particularly narrow implant, which can be introduced through an also narrow corneal incision (entrance) into the cornea, in an intermediate state, it is provided in one embodiment of the invention that a freely defined line L along the circumference in the starting state is pivoted after compression with the compression force F to form a line L' along the circumference in the intermediate state, wherein the length of L' is greater than L.

This extension of the length L' is achieved by the use of a (pseudo-)elastic material during the production of the implant. If an elastic material is provided, in addition a stretching of the implant is achieved by the rotation in the pivotable longitudinal section, whereby the length L' is longer than the original length L. This extension also causes easier deformability of the implant, whereby the implant has even smaller lateral dimensions for an implantation in the cornea of the eye.

To achieve particularly suitable lateral dimensions of the implant for the implantation in the cornea, it is provided in one embodiment of the invention that the compression of the implant achieved by the compression force in the force direction, without breaking through along the implant cross-section, is at least 5%, better at least 10%, and ideally at least 20% depending on material and geometry.

To achieve particularly suitable lateral dimensions of the implant for the implantation in the cornea, it is provided in one embodiment of the invention that a rotation of the implant cross-section of the implant by application of the compression force takes place at least in sections by the angle α of at least 1°, preferably at least 2°, particularly preferably at least 3°, and ideally at least 5°.

Of course, an implant which in an intermediate state has a rotation by the angle α of less than 1° or more than 5° is not precluded.

BRIEF DESCRIPTION OF THE FIGURES

The invention will be explained in more detail on the basis of exemplary embodiments. The drawings are examples and are to illustrate the concept of the invention, but are in no way to restrict it or even reproduce it exhaustively.

In the figures.

WAYS OF EMBODYING THE INVENTION

Figure 1:
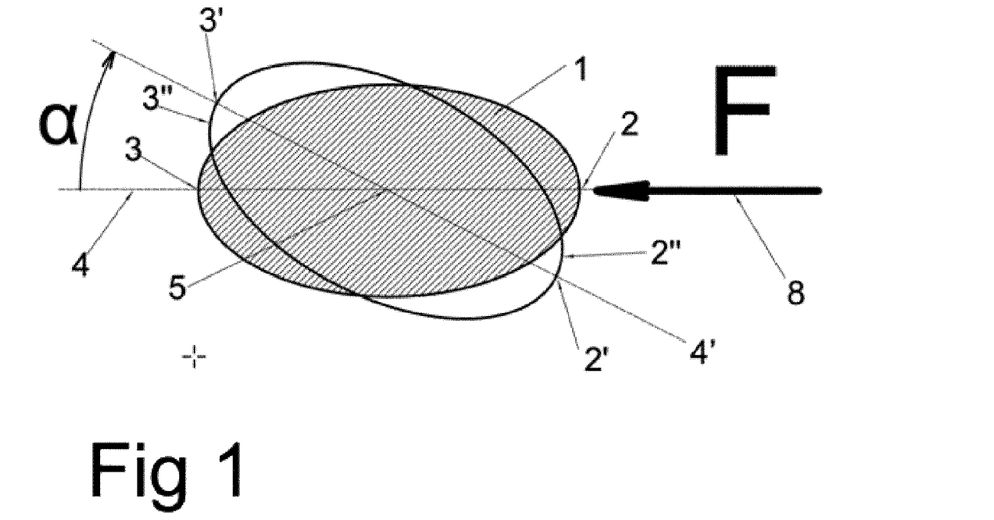
FIG. 1 shows a pivot of the implant cross-section 1 by exertion of a compression force F in the intermediate state

FIG. 1 shows an implant according to the invention comprising an arbitrary implant cross-section 1, which is oval here. The shaded area shows the implant cross-section 1 in the starting state. The ring-shaped implant (also referred to as a ring), which can in principle have any arbitrary implant cross-section 1 (also referred to as a cross-sectional area), is embodied so that it has a very specific shape memory. The shape memory of the implant can be achieved by the material used or the geometric properties or the internal structure or a special processing (for example temperature treatment) or a combination thereof.

To be able to use such materials for the purpose according to the invention, it is necessary to find and use further degrees of freedom of the deformation which increase the deformability and the breaking strength upon deformation. In the present disclosure, a compression force F is converted into a deformation of the implant so that a pivot of the implant around a circumferential axis (longitudinal axis) 5 enables the compression of the implant to a sufficiently small lateral dimension without the implant breaking at the same time, whereby an implantation of the implant into the cornea through a narrow wound opening is made possible.

The pivot at least in sections of the implant body along or around a circumferential axis 5 into the intermediate state by application of a compression force F is achieved here in that a shape memory is applied to the implant body at least in sections, preferably during the manufacturing, which ensures that upon application of a compression force F, the desired pivot of the implant body, preferably around a circumferential axis 5, takes place at least in sections. This can be produced by a mechanical, thermal, electrical, or another physical or chemical treatment of the material or the implant, preferably, but not necessarily during the production. The implant can be manufactured in principle from any material including plastic, metal, semiconductor, insulator, ceramic, biological materials (for example collagen), etc., which enables such a treatment. Thus, for example, in the case of a polymer plastic, the alignment or arrangement or size distribution of the polymer molecules can be embodied in such a way that an externally applied compression force F results in a force distribution in the interior of the implant, from which the desired pivot of the implant body results. In this case, for example, the arrangement or alignment or size distribution of the polymer molecules can also vary along the circumference or within the implant cross-section 1 at least in sections along the circumference. Thus, for example, the alignment of the polymer molecules can be embodied at least in sections in parallel to or circularly around a circumferential axis 5. Furthermore, for example, the desired pivot can also be achieved by variation of the material density along the circumference or over the cross-section. Materials which may, for example, by a second-order phase transition (martensitic phase transition), have a specific shape applied by thermal or other physical treatments with application of a compression force in the meaning of a shape memory material and in the case of which the pivot is triggered in the application by applying a corresponding compression force F are also conceivable.

The implant cross-section 1 of the implant can be arbitrary in each case, for example, circular, oval, as a polygon with or without rounded edges, convex on one side and straight or concave on the other, etc. (cf. FIGS. 1, 2a, and 2b, FIG. 6). The implant can be curved arbitrarily along a circumferential axis 5 (also referred to as axis, center line, center axis, body axis, or longitudinal axis) of the implant. However, this body or circumferential axis 5, in the starting state, preferably follows a constant curvature around the axis of symmetry 9 (also referred to as axis of rotation) having an arc length of 360°. The implant can have a variable or homogeneous cross-section along this circumferential axis 5. In the case of a homogeneous implant cross-section 1, the cross-sectional shape, the alignment of the implant cross-section 1 to the implant plane 8, and the size of the cross-sectional area along the circumference are all equal.

Figure 2:
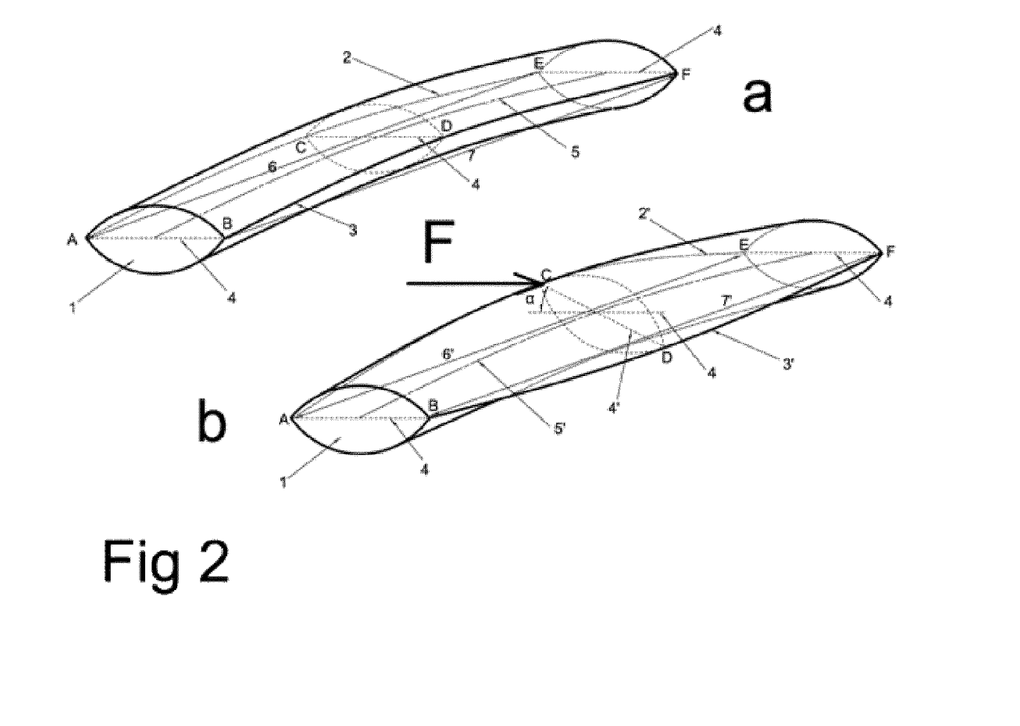
FIG. 2a shows the conditions in a sectoral illustration of the implant in the starting state
FIG. 2b shows the conditions in a sectoral illustration of the implant in the intermediate state

The shape memory of the implant is distinguished by the possible adjustment into at least two, preferably three states, which can be converted into one another by an external signal (for example compression force F), wherein FIG. 2a shows an implant according to the invention in the starting state and FIG. 2b shows an implant according to the invention in the intermediate state. The end state does not necessarily but preferably in turn essentially corresponds to the starting state, which is shown in FIG. 2a:

1. Starting state is the state in which the implant is designed as a ring implant which is arranged rotationally symmetrical around an axis of symmetry 9 and has an arc length of at least 350° and ideally 360° (shown in FIG. 2a). The implant will generally be planar in this state, i.e., the implant plane is a planar surface.
2. Intermediate state is the state in which a lateral compression of the rigid implant in the force direction of at least 5%, better at least 10%, and ideally at least 20% may be achieved by the application of a compression force (transverse force) F in an engagement point 13, without the implant breaking, in that a pivot of the alignment of the implant cross-section 1 by an angle α around a circumferential axis 5 is triggered (shown in FIG. 2b). This pivot by the angle α is preferably to be at least 1°, preferably at least 2°, still more preferably at least 3°, and ideally at least 5°. Due to the pivot of the implant cross-section 1 or its orientation it is possible to compress an implant which is rigid per se so that it can be implanted via the smallest possible wound opening in the cornea without the implant breaking.
3. End state is the state in which the implant is transferred by removal of the force F into a geometric state in which it can correct the refractive power of the cornea in the best possible manner. The geometry of the end state of the implant can correspond here to that of its starting state.

FIG. 2a shows an implant according to the invention in the starting state. The implant plane 8 can be defined in the starting state in various ways depending on the embodiment. The implant plane 8 can thus be defined by the curved outer edge 2 between two points A and E separated from one another. This outer edge 2 extends between or along the points A, C, and E. In this case, the implant plane 8 is the plane in which this outer edge 2 extends or it is spanned by the points A, C, and E which are located along this outer edge 2. The implant plane 8 can also be defined by the curved inner edge 3 between two points B and F separated from one another. This inner edge 3 extends between or along the points B, D, and F. In this case, the implant plane 8 is the plane in which the inner edge 3 extends or is spanned by the points B, D, and F which are located along this inner edge. The implant plane 8 is, at least in the starting state, perpendicular to the axis of symmetry 9 of the implant.

Figure 3:
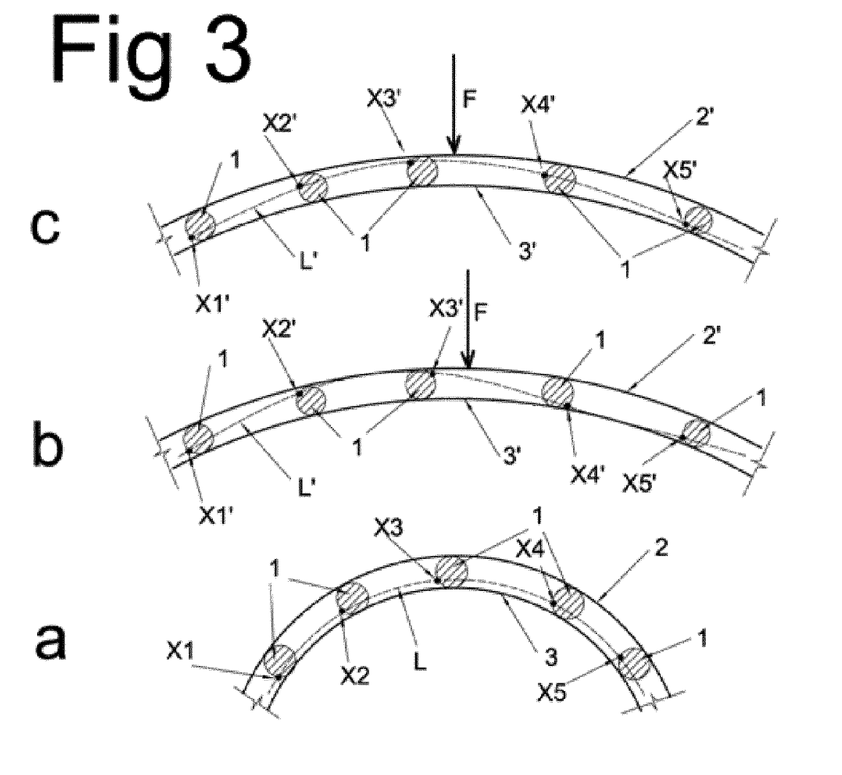
FIG. 3a shows a circumferential line L in the starting state of the implant
FIG. 3b shows the pivot of the circumferential line L into L' in an exemplary intermediate state of the implant
FIG. 3c shows the pivot of the circumferential line L into L' in another exemplary intermediate state of the implant

FIGS. 3a-c show, on the basis of the surface points X1-X5, the rotation of the implant cross-section 1 caused by an acting compression force F, wherein FIG. 3a shows a section of a ring-shaped implant in the starting state, while FIGS. 3b and 3c show the implant in an intermediate state.

If a compression force F of preferably greater than 1 mN or greater than 10 mN and if possible less than 1.5 N is exerted on the implant in the starting state, the force direction of which is preferably in the implant plane 8, the ring-shaped geometry of the implant deforms into a shape deviating from the ring shape, preferably a substantially oval shape, and a pivot of the implant cross-section 1 by an angle α additionally occurs, at least in one ring region, but preferably in the one where the force F is applied. The direction of the pivot can be both clockwise and also counterclockwise. The pivot can act along a specific longitudinal section of the implant and thus extend the actual circumference, which has a specific neutral circumferential line L before application of the compression force, into L'. The surface points X1 to X5 originally extending on the neutral ring-shaped circumferential line L then extend as X1' to X5' along a spiral-shaped circumferential line L'. A circumferential line L which is previously circular at least in segments becomes a circumferential line L' which is spiral-shaped at least in segments here. In this way, the compression force F (also referred to as external force F) is converted at least in sections into an elastic rotational energy along a circumferential axis 5, whereby a further degree of freedom of the deformation results, whereby the risk of breaking during the implantation is reduced. In other words: If an implant made of sufficiently rigid material which is necessary to apply a specific shape for the refractive force correction to the cornea were simply only compressed, it would not be possible to compress the implant to the required extent without it breaking. In particular in the longitudinal region 14, the ring region which is located 90° to the direction of the force action, a bending strain would occur which would very rapidly result in a material break in the longitudinal region 14. This compaction in the inner region and the tension in the outer region of the longitudinal region 14 is opposed in compensation by the present invention by a pivot and thus lengthening of the circular circumferential lines, whereby the tension in the longitudinal region 14 and thus the risk of breaking is reduced.

The (elastic) pivot energy stored in the intermediate state by the application of the compression force F in the pivot of the implant cross-section 1 causes, upon removal of the compression force F, a restoring force F' of at least 0.1 mN against the original force direction to relax the compressed lateral dimension of the implant into an end state. Depending on the material, geometry, and processing, this restoring force F' can be up to 1 N and greater. The energy transferred to the implant by the compression force F due to the occurring compression is partially converted into an elastic pivot energy of the implant cross-section 1 and stored in the intermediate state. By removing the external force F, this pivot energy in the implant cross-section 1 is released as the restoring force F', which puts the implant cross-section 1 into an end state, the geometry of which preferably essentially corresponds to that of the starting state.

Figure 4:
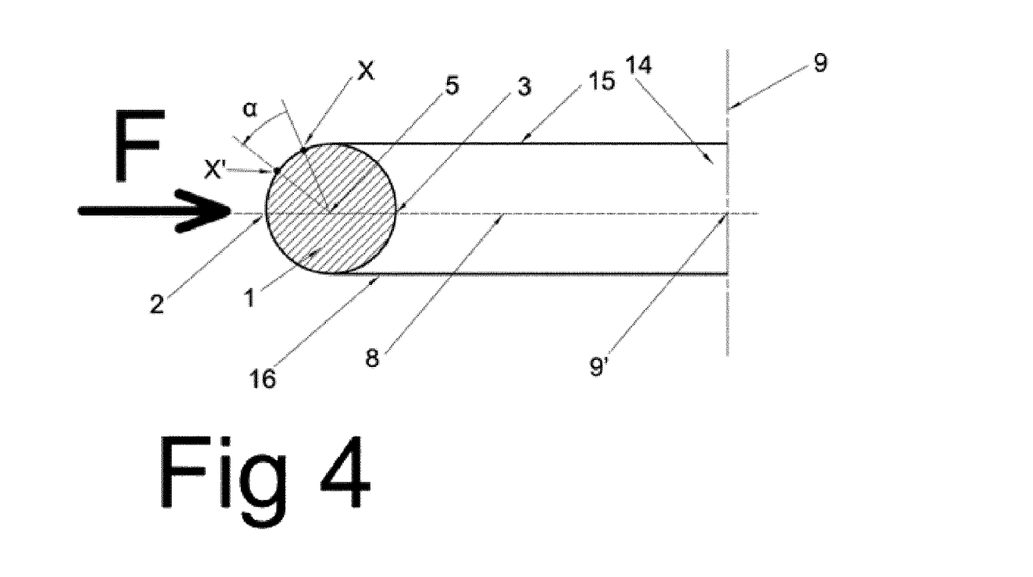
FIG. 4 shows the pivot of the implant cross-section on the basis of the pivot of an arbitrary point X on the surface of the implant in the starting state by the angle α into the position X' into the intermediate state

FIG. 4 shows a preferred embodiment of the invention, wherein the rotation of a point X by an angle α to a point X' is illustrated on the basis of a section of an implant according to the invention. An even more space-saving geometry of the implant is achieved by a force action of the compression force F according to FIG. 4. The combination of the obtained degree of freedom from the pivot with the pivot energy thus stored in the implant cross-section 1 and the obtained degree of freedom from the deflection of the longitudinal region 14 out of the implant plane 8 with the deflection energy thus stored in the implant cross-section 1 enables a particularly advantageous deformation of the implant to even smaller lateral dimensions by the compression force F, whereby particularly favorable surgical conditions are enabled for the implantation of the implant in the cornea through a narrow wound opening.

Particularly good conditions are achieved in this case if the compression force F perpendicular to the tangent 12 of the implant cross-section 1 is exerted at the application point 13 (also referred to as the engagement point of the force) in the implant plane 8. However, at least a part of the compression force F is to be applied along a force direction in the implant plane 8. FIGS. 2a and 2b show that the connecting line 4, which lies between the original outer edge 2 and inner edge 3 or between points on the outer edge 2 and the inner edge 3, can be adjusted pivoted by the angle α in relation to the connecting line 4' between 2' and 3' in relation to the original alignment of 4 or relative to the force direction or relative to the axis of symmetry 9 or relative to the original implant plane 8 or any arbitrary other defined direction. Due to the exertion of a compression force F, an arbitrary point X on the surface of the implant pivots by the angle α to the point X', at least preferably in the section of the implant where the compression force F is applied, as shown in FIG. 4. In particular, due to application of a compression force F to the implant, at least one component of the force direction which lies in the implant plane 8 and at least one component of which is directed to the center point 9' of the implant or perpendicular to the tangent 12 at the application point 13 of the outer edge 2, the implant cross-section 1 adjusts itself pivoted by the angle α around a circumferential axis 5, so that a point X on the surface of the implant or on the boundary of the implant cross-section 1 travels by the angle α into a position X' relative to an arbitrary reference point of the implant.

Figure 5:
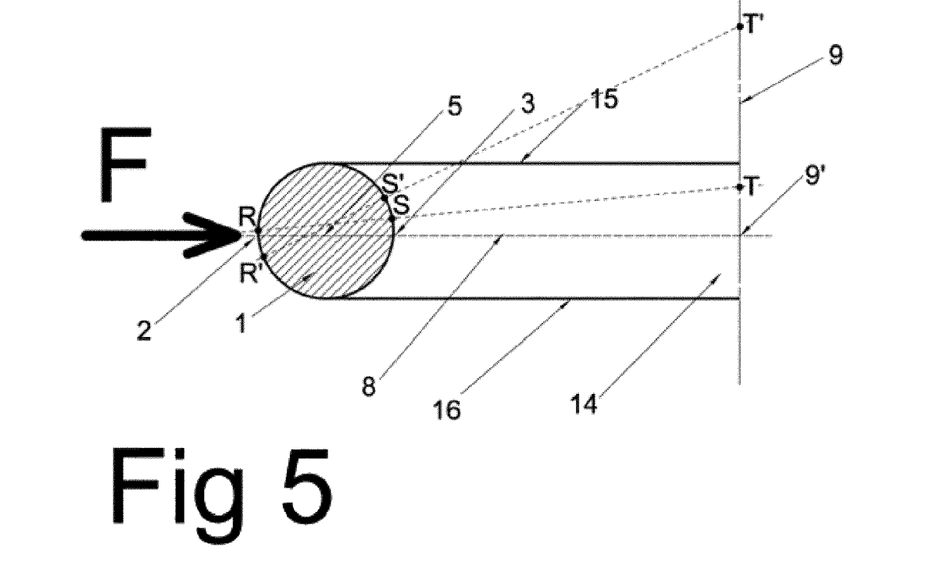
FIG. 5 shows the pivot of the implant cross-section on the basis of the pivot of a connecting line between two surface points R and S into the positions R' and S'

FIG. 5 shows, in other words: A straight line which extends through two different surface points R and S of the implant cross-section 1 and a point T which lies on the axis of symmetry 9 pivots by exertion of a compression force F on the implant cross-section 1 by an angle α into a straight line which extends through the surface points R' and S' corresponding to R and S. R' and S' represent here the positions of the surface points R and S pivoted by the angle α on the surface of the implant cross-section 1 after exertion of the compression force on the implant body. An extension of the connecting line of the pivoted surface points R' and S' does not necessarily have to intersect the axis of symmetry 9. In addition, the pivot point of the pivot does not necessarily have to correspond to the circumferential axis 5.

As described above, FIG. 4 shows a section of an implant according to the invention, wherein the implant has an implant cross-section 1, which implant cross-section 1 is the sectional surface through the implant which lies in a plane which at least in the starting state is perpendicular to the implant plane 8 and in which or in parallel to which the axis of symmetry 9 extends. In other words, the implant cross-section 1 is a sectional surface of the implant which lies in a plane perpendicular to the implant plane 8 and which is delimited by an outer edge 2 and an inner edge 3. The connecting line 4 lies between the outer edge 2 and the inner edge 3 viewed in the direction of a diameter line of the implant (i.e., the line within which the greatest possible distance lies between two points on the outer edge 3 or lies between two points on the inner edge 2 and which therefore preferably extends through the center point 9'). Due to the exertion of a compression force F on the implant cross-section 1, a state change toward an intermediate state is triggered in this way, wherein the compression of the implant in the force direction permits the implant cross-section 1 of the implant to pivot by an angle α at least in sections and preferably at the engagement point 13 of the force F on the implant relative to the alignment of the implant cross-section 1 before the force transmission. This pivot of the implant cross-section 1 by an angle α is shown in FIG. 1 and in FIG. 6. The surface point X thus travels to the position X'—pivoted by the angle α (cf. FIG. 6).

FIG. 5 shows that the pivot of the implant cross-section 1 due to the force F takes place, however, in such a way that an extension of the connecting line between R' and S' also intersects the axis of symmetry 9 in a point T'. Particularly good conditions result if at least one component of the force direction of F lies in the implant plane 8 and at least one component is directed toward the center point 9' of the implant or perpendicular to the tangent 12 at the engagement point 13 of the outer edge 2. The points R and S are then located on the surface (boundary or the edge) of the cross-sectional surface (cross-section) through the implant cross-section 1 on which an engagement point 13 of the force F is also located.

Figure 6:
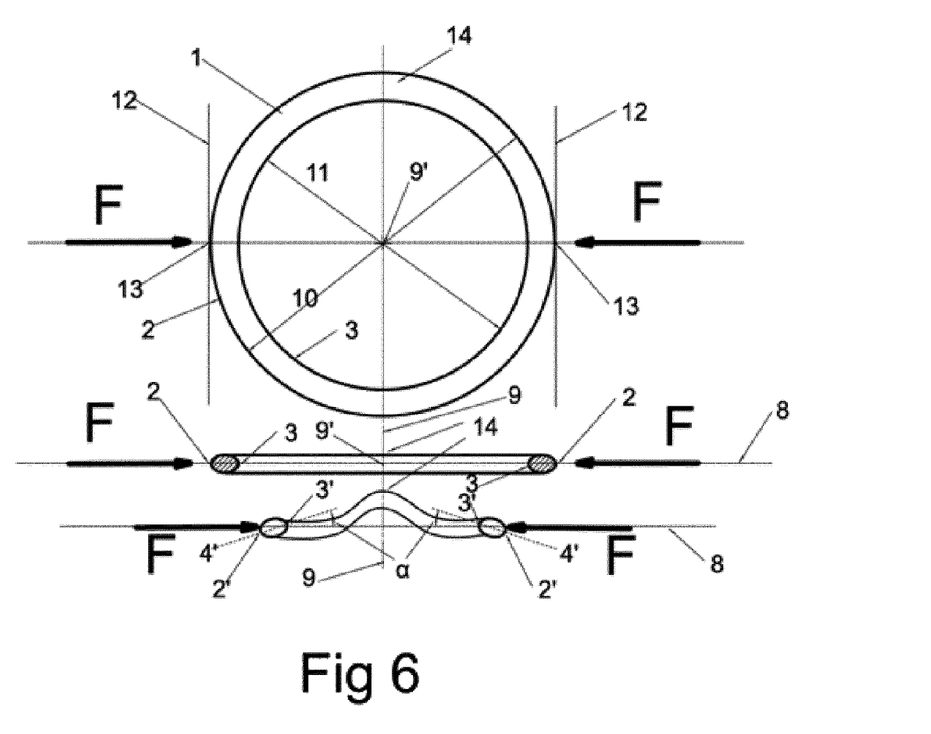
FIG. 6 shows the implant in various views in the starting state and in the intermediate state

FIG. 6 shows the conditions in the starting state and in the intermediate state under specific and different conditions. FIG. 6 shows, in the uppermost illustration, a top view of the ring-shaped implant in the starting state, in the middle image the implant, which is in the starting state and is cut in the middle, in a side view, and the lower image shows the implant in the intermediate state. FIG. 6 discloses a ring-shaped implant, wherein the implant is circular in the starting state. The (convex) boundary curved away from the implant body 1 represents the outer edge 2.

This boundary line has, in the case of a regular curvature of the implant around the axis of symmetry 9, the greatest length measured in millimeters. The (concave) boundary curved toward the implant body 1 represents the inner edge 3. This boundary line has, in the case of a regular curvature of the implant around the axis of symmetry 9, the least length measured in millimeters. In other words, the outer edge 2 is represented by the boundary line of the implant which always measures the greatest distance from the center point 9' of the implant along the circumference. Accordingly, the inner edge 3 is represented by the boundary line of the implant which always measures the least distance from the center point 9' of the implant along the circumference.

At least for the starting state, the following applies: The circumference, measured along the outer edge 2, is as much as possible not to exceed 30 mm. The inner diameter 11 is as much as possible to be greater than 3 mm and less than 10 mm. The distance between the inner edge 2 and the outer edge 3 (also referred to as the ring width) measured along a diameter line is to be as much as possible less than 1.5 mm, better less than 1 mm, and ideally less than 0.7 mm. The height of the implant is the greatest distance between 2 (opposing) surface points measured in the direction of the axis of symmetry 9 and is between 50 µm and 500 µm. The diameter line extends as a straight line between two points on an outer edge or inner edge and also includes the center point of the implant 9' or at least a point of the axis of symmetry 9.

The middle and bottom illustrations of FIG. 6 show that it additionally can be possible to trigger a deformation of the implant by the compression force F in such a way that in the longitudinal region (ring section) 14 of the implant which is located perpendicular to the direction of the compression force F, the implant cross-section 1 or the corresponding cross-section is deflected out of the original planar or two-dimensional implant plane 8 in a third dimension. Upon application of the compression force F, instead of a solely oval implant shape, a substantially saddle-shaped body thus results (shown at the very bottom in FIG. 6). The straight and two-dimensional implant plane 8 of the starting state, in which the inner edge 3 or the outer edge 2 lies, and in which state the inner edge 3 and the outer edge 2 enclose a planar surface, is thus transferred into an intermediate state, in which intermediate state an arched (curved) surface results, which extends in all three directions, in which the inner edge 3 and the outer edge 2 delimit a substantially saddle-shaped surface (shown at the bottom in FIG. 6). The deflection of the longitudinal region 14, which is orthogonal to the force direction, out of the two-dimensional ring plane 8 of the starting state is at 90° to the force direction or takes place in the direction of the axis of symmetry 9. In this case, at least a part of the compression force F is converted into the elastic energy of the deflection of the longitudinal region 14 and stored in the intermediate state. In other words: If an implant made of sufficiently rigid material which is necessary to apply a specific shape for the refractive force correction to the cornea were simply only compressed, the implant would break. In particular in the longitudinal region 14, which is located 90° to the force action, a bending strain would occur which would also very rapidly result in a material break there. Due to the deflection of the implant because of the shape memory in the longitudinal region 14 out of the original ring plane 8 (also referred to as the implant plane) in the third dimension, this compaction in the inner region and the tension in the outer region of the longitudinal region 14 (also referred to as ring region and ring section) is opposed in compensation by a relaxation by dissipation of the tension differences between tension and compaction lines, whereby the tension in the longitudinal region 14 in general and thus the risk of breaking are reduced. In addition, due to the application of a compression force F, a further degree of freedom is additionally also obtained, in that the implant is embodied so that the implant cross-section is pivoted, at least in a longitudinal section (in sections) in relation to the starting state by the angle α. In one embodiment, due to the application of a compression force F at the engagement point 13 of the implant, both a pivot of the implant cross-section in a pivotable longitudinal section (in sections along the circumference) and also a deflection of the implant body 1 in an implant section (longitudinal region) 14, which is located 90° to the force action, in the direction of the axis of symmetry 9 out of the implant plane 8 is enabled.

In all embodiment variants and examples of the present invention, the compression force F can consist of two components of equal size oriented opposite to one another, which are applied at opposing engagement points 13 of the implant, as shown in FIG. 6, for example. That is to say, the connecting line between the opposing force components F extends through the center point 9'.

Due to the properties according to the invention, the implant obtains increased deformability (compressibility) in an intermediate state, which enables the implant to be implanted through a narrow wound opening. After the implantation in the cornea, in which the implant is in the intermediate state, through a narrow wound opening, upon removal of the compression force F, a restoring force F' results, which is oriented at least partially against the original force direction and which puts the implant into an end state by independent unfolding. The independent unfolding from an intermediate state into an end state is at least partially the result here of the conversion of the (elastic) pivot energy stored in the implant cross-section 1 by the application of the compression force F into a restoring force F'. The geometry of the starting state preferably substantially corresponds to that of the end state.

It is especially explained that each described embodiment or each example or each property can be combined to form a further valid embodiment.

LIST OF REFERENCE SIGNS 1 implant cross-section
2 outer edge without force action
2' outer edge with force action
3 inner edge without force action
3' inner edge with force action
4 connecting line between outer edge 2 and inner edge 3 without force action
4' connecting line between outer edge 2 and inner edge 3 with force action
5 circumferential axis
6 connecting line between 2 selected points of the outer boundary without force action
6' connecting line between 2 selected points of the outer boundary with force action
7 connecting line between 2 selected points of the inner boundary without force action
7' connecting line between 2 selected points of the inner boundary with force action
8 implant plane
9 axis of symmetry of the implant
9' center point of the implant
10 outer ring diameter
11 inner ring diameter
12 tangent of the implant which lies perpendicular to the direction of a diameter
13 engagement point of the compression force on the implant perpendicular to the tangent 12
14 longitudinal region which is located 90° to the direction of the force action
15 upper edge
16 lower edge
F compression force (external force)
F' restoring force X surface point before deformation X' position of the surface point X after deformation L connection between the surface points X (X1, X2, X3, X4, X5) along the circumference of the implant without force action L' connection between the surface points X (X1', X2', X.3', X4', X5') along the circumference of the implant with force action T, T' points on the axis of symmetry 9

R, S position of surface points on the implant before force action, the extended connecting line of which intersects with the ring axis 9 at a point T R', S' position of the surface points R, S on the implant after force action α pivot angle of the cross-sectional area due to the force action (angle)

The invention claimed is:

1. A ring-shaped corneal implant having shape memory for implantation in the cornea of the eye, wherein the implant spans an implant plane (8) in a starting state, and wherein the implant is transferable by application of a compression force (F) in the implant plane (8) from a starting state into an intermediate state, in which lateral dimensions of the implant, measured in the force direction, are smaller than lateral dimensions of the implant in the starting state, wherein an alignment of an implant cross-section (1) in the intermediate state is pivoted at least in one pivotable longitudinal section along a circumference of the implant by an angle (α) around a circumferential axis (5) of the corneal implant in relation to the starting state, wherein the corneal implant is both geometrically and mechanically closed and does not have a discontinuity, wherein the corneal implant is formed from a polymer plastic comprising polymer molecules, and wherein the corneal implant has a specific arrangement and/or alignment and/or size distribution of polymer molecules at least in sections along the circumference of the corneal implant, wherein after releasing the compression force the implant changes its shape from the intermediate state into an end state where the end state corresponds to the starting state, and wherein the ring-shaped corneal implant has a modulus of elasticity of at least 1000 MPa.

2. The implant according to claim 1, wherein a pivotable longitudinal section of the implant is located in the region of an engagement point (13) of the compression force (F).

3. The implant according to claim 1, wherein a pivotable longitudinal section is located along the circumference of the implant outside an engagement point (13) of the compression force (F).

4. The implant according to claim 1, wherein the implant has two pivotable longitudinal sections opposite to one another in the implant, the implant cross-sections (1) of which are each pivoted in the intermediate state by an angle (α) in relation to the starting state.

5. The implant according to claim 1, wherein a pivotable longitudinal section extends at least over 5° along the circumference of the implant.

6. The implant according to claim 1, wherein the implant is manufactured from a biocompatible polymer material.

7. The implant according to claim 1, wherein the alignment of polymer molecules is at least in sections not in the direction of the circumferential axis (5) of the implant.

8. The implant according to claim 1, wherein the alignment of polymer molecules is at least in sections in the direction of the circumferential axis (5).

9. The implant according to claim 1, wherein the implant has a material density, which material density varies along the circumference of the implant and/or over the implant cross-section (1), so that the material density is different in one pivotable longitudinal section of the implant from another longitudinal section of the implant.

10. The implant according to claim 1, wherein the implant has, along the circumference of the implant in at least one longitudinal section of the implant, an implant cross-section (1) deviating from rotational symmetry, so that the implant cross-section (1) is different in one pivotable longitudinal section of the implant from another longitudinal section of the implant.

11. The implant according to claim 1, wherein the implant is embodied in the starting state as a complete ring having uniform implant cross-section (1) along the circumference of the implant rotationally symmetrical around an axis (9) perpendicular to the implant plane (8).

12. The implant according to claim 1, wherein the implant has an inner edge (3), which inner edge delimits a surface, wherein the surface delimited by the inner edge (3) is planar in the starting state and is curved in the intermediate state.

13. The implant according to claim 1, wherein the compression of the implant in the force direction achieved by the compression force (F), without breaking through along the implant cross-section (1), is at least 5%.

14. The implant according to claim 1, wherein a rotation of the implant cross-section (1) of the implant by application of the compression force (F) takes place at least in sections by the angle α of at least 1°.

* * * * *